United States Patent [19]
Brooks et al.

[11] Patent Number: 5,256,372
[45] Date of Patent: Oct. 26, 1993

[54] DIPSTICK TEST DEVICE INCLUDING A REMOVABLE FILTER ASSEMBLY

[75] Inventors: Paul C. Brooks, Portland; Erwin F. Workman, Cape Elizabeth; Quentin J. Tonelli, Portland, all of Me.

[73] Assignee: Idexx Corporation, Portland, Me.

[21] Appl. No.: 446,009

[22] Filed: Dec. 5, 1989

Related U.S. Application Data

[63] Continuation-in-part of Ser. No. 118,750, Nov. 6, 1987, abandoned.

[51] Int. Cl.$^5$ ............................................. G01N 21/78
[52] U.S. Cl. .................................... 422/58; 422/60; 422/61; 422/101; 436/518; 436/165; 436/170; 436/178; 436/805; 436/807; 436/810
[58] Field of Search ............... 436/514, 518, 528, 165, 436/169, 170, 177, 178, 805, 807–810; 422/56–61, 101, 102, 99

[56] References Cited

U.S. PATENT DOCUMENTS

| | | |
|---|---|---|
| 2,986,497 | 5/1961 | Pagano et al. . |
| 3,197,384 | 7/1965 | Goldman . |
| 3,552,925 | 1/1971 | Fetter . |
| 3,645,687 | 2/1972 | Nerenberg . |
| 3,770,380 | 11/1973 | Smith . |
| 3,825,410 | 7/1974 | Bagshawe . |
| 3,839,153 | 10/1974 | Schuurs et al. . |
| 3,888,629 | 6/1975 | Bagshawe . |
| 3,891,507 | 6/1975 | Brewer . |
| 3,951,748 | 4/1976 | Devlin . |
| 3,990,852 | 11/1976 | Piazzi et al. . |
| 4,002,532 | 1/1977 | Weltman et al. . |
| 4,055,394 | 10/1977 | Friedman et al. . |
| 4,059,405 | 11/1977 | Sodickson et al. . |
| 4,066,511 | 1/1978 | Montagnon . |
| 4,066,512 | 1/1978 | Lai et al. . |
| 4,090,850 | 5/1978 | Chen et al. . |
| 4,111,754 | 9/1978 | Park . |
| 4,146,365 | 5/1979 | Kay et al. . |
| 4,157,895 | 6/1979 | Finlay et al. . |
| 4,168,146 | 9/1979 | Grubb et al. . |
| 4,200,690 | 4/1980 | Root et al. . |
| 4,205,058 | 5/1980 | Wagner et al. . |
| 4,226,978 | 10/1980 | Boguslaski et al. . |
| 4,233,402 | 11/1980 | Maggio et al. . |
| 4,246,339 | 1/1981 | Cole . |
| 4,270,920 | 6/1981 | Kondo . |
| 4,330,627 | 5/1982 | Thomas et al. . |
| 4,331,650 | 5/1982 | Brewer et al. . |
| 4,363,874 | 12/1982 | Greenquist . |
| 4,365,970 | 12/1982 | Lawrence . |
| 4,366,241 | 12/1982 | Tom . |
| 4,376,110 | 3/1983 | David et al. . |
| 4,407,943 | 10/1983 | Cole et al. . |
| 4,424,279 | 1/1984 | Bohn et al. . |
| 4,486,540 | 12/1984 | Brewer . |
| 4,517,288 | 5/1985 | Giegel et al. . |
| 4,541,987 | 9/1985 | Guandagno . |

(List continued on next page.)

FOREIGN PATENT DOCUMENTS 0327395  8/1989  European Pat. Off. .

OTHER PUBLICATIONS

Weiss and Blankstein, American Clinical Products Review, May/Jun. (1987).

Bangs, American Clinical Products Review, May/Jun. (1987).

Primary Examiner—Robert J. Hill, Jr.

[57] ABSTRACT

Disclosed is a dipstick test device for detecting an analyte in a liquid sample by treating the analyte with at least one liquid reagent to form a detectable reaction product. The device includes: a) an aqueous impermeable, aqueous insoluble reaction zone, adapted to retain the detectable reaction product; and b) a control absorbent above, and in liquid-transferring relation with, the reaction zone. The control absorbent has a predetermined, limited liquid-absorbing capacity, and the dipstick is sized and configured for insertion into a vessel containing the sample, with the control absorbent oriented above the reaction zone, so that the control absorbent fills to capacity with sample and the reaction zone incubates with the sample. The device may further include an absorbent reservoir which can be moved into liquid transferring contact with the reaction zone.

19 Claims, 8 Drawing Sheets

U.S. PATENT DOCUMENTS

| | | |
|---|---|---|
| 4,578,358 | 3/1986 | Oksman . |
| 4,578,359 | 3/1986 | Oksman et al. . |
| 4,587,221 | 5/1986 | Cais et al. . |
| 4,623,461 | 11/1986 | Hossom . |
| 4,632,901 | 12/1986 | Valkirs . |
| 4,665,034 | 5/1987 | Chandler . |
| 4,690,801 | 9/1987 | Anderson . |
| 4,717,656 | 1/1988 | Swanljung . |
| 4,727,019 | 2/1988 | Valkirs . |
| 4,797,260 | 1/1989 | Parker . |
| 4,909,992 | 3/1990 | Bjorkman ............ 422/101 XR |
| 4,939,096 | 7/1990 | Tonelli ............ 435/5 |
| 4,959,197 | 9/1990 | Parekh et al. ............ 422/101 |
| 4,980,298 | 12/1990 | Blake et al. ............ 422/61 |
| 5,008,080 | 4/1991 | Brown et al. ............ 422/101 X |

POSITION A
FIG. 7a

POSITION B
FIG. 7b

DIPSTICK TEST DEVICE INCLUDING A REMOVABLE FILTER ASSEMBLY

This application is a continuation-in-part of my earlier co-pending application Ser. No. 118,750, filed Nov. 6, 1987, now abandoned which is hereby incorporated by reference.

BACKGROUND OF THE INVENTION

This invention relates to devices and methods for detecting an analyte, for example, using an immunoassay.

An analyte in a sample may be detected by treating the sample with various reagents, such as labeled immunological binding partners to the analyte and reagents to enable detection of the label. Often, the sample must be washed between administration of various reagents.

An accurate assay may depend on controlling the amount of reactants exposed to the sample and the duration of the reactions taking place. It is desirable to control these variables in a way that enables use of the assay kit by individuals of widely varying skill and experience, so that variations in individual technique do not materially alter the result. Consistency and accuracy can be difficult, particularly when a color generating indicator must be evaluated against a background. Test reagents should be tested to verify their activity, which may erode over time. Also, it is desirable to reduce the time necessary to perform the assay. It is desirable to have the ability to assay extremely small sample volumes with relative low concentrations of analyte, and/or to detect relatively small differentials in analyte concentration. Finally, it is desirable to assay whole blood samples without complex centrifuging equipment.

One method for adding and washing reagents in an immunoassay uses an absorbent material to move liquid washes and reagents through a solid substrate (such as a membrane) to which other reactants are immobilized.

Cole et al. U.S. Pat. No. 4,246,339, discloses an immunoassay test device including sorbent material for drawing liquid through a microporous membrane at the bottom of a test well. The sorbent material is resiliently biased away from the membrane, and it draws liquid through the membrane only when the two are forced together to overcome the bias. Sorbent material comprises a surface layer which is hydrophobic and a bulk portion which is wettable. Reagents are added serially to the test well and, after each reagent has been in the well for a prescribed time, the membrane and sorbent material are forced together to draw off liquid before the next reagent is added.

Tom U.S. Pat. No. 4,366,241, discloses an immunoassay device having two bibulous zones, an analyte binding partner being non-diffusively fixed in the first zone (the "immunoabsorbing zone") and the second layer being a reservoir zone, either directly or indirectly in liquid-receiving relationship with the first zone to pull liquid through and out of the first zone throughout the duration of the assay. The immunoabsorbing zone is an exposed portion of a flat test strip which is otherwise covered by a protective coating.

Hossom U.S. Pat. No. 4,623,461, discloses a test device having a filter which feeds a specimen to a flat absorbent material having a reaction zone surrounded by peripheral zone. An annular ring of absorbent material is positioned around the peripheral zone, so that fluid is drawn radially outward from the reaction zone, through the peripheral zone, and into the absorbent material.

Bagshawe U.S. Pat. No. 3,888,629, discloses an assay device having a matrix pad which may be pre-treated with a binding partner for the analyte being assayed. Absorbent material is forced into intimate contact with matrix pad to increase the speed of filtration through the matrix pad.

Kondo U.S. Pat. No. 4,270,920, discloses multiple reagent layers arranged on a single horizontal support. A porous spreading layer spreads the sample as it moves into the reagent layers, so that a relatively small sample volume will be spread evenly over the reagent layers.

Lawrence U.S. Pat. No. 4,365,970, Oksman U.S. Pat. No. 4,578,358, Brewer U.S. Pat. No. 4,486,540, and Guandagno U.S. Pat. No. 4,541,987, disclose test devices comprising positive and negative control spots on a test pad or slide.

Applicants' assignee, Idexx Corporation (formerly Agritech Systems, Inc.), has marketed an immunoassay device comprising positive and negative control spots. Separation of the spots is maintained by spotting the reagents a sufficient distance from each other.

Various companies have marketed self-contained immunoassays using a membrane as a solid support (e.g. Syntex's AccuLevel and Hybritech's ICON). See Valkirs U.S. Pat. Nos. 4,632,901 and 4,727,019. See also, Weiss and Blankstein, *American Clinical Products Review*, May/June (1987). Latex particles, to which ligands have been attached, have been used in aqglutination assays Bangs, *American Clinical Products Review*, May/June (1987).

SUMMARY OF THE INVENTION

One aspect of the invention generally features a dipstick test device for detecting an analyte in a liquid sample by treating the analyte with at least one liquid reagent to form a detectable reaction product. The test device includes two components: a) means defining an aqueous permeable, aqueous insoluble reaction zone, adapted to retain the detectable reaction product; and, integral with or separate from the reaction zone, b) a control absorbent above, and in liquid-transferring relation with, the means defining a reaction zone The control absorbent has a predetermined, limited, liquid-absorbing capacity. The dipstick is sized and configured for insertion in a vessel containing the sample, with the control absorbent oriented above the means defining a reaction zone, so that the control absorbent fills to capacity and the means defining a reaction zone incubates with the sample.

A second aspect of the invention also features a test device for detecting an analyte in a liquid sample by treating the analyte with at least one liquid reagent to form a detectable reaction product. The device of the second aspect includes: a) means defining an aqueous permeable, aqueous insoluble reaction zone, adapted to retain the detectable reaction product; b) an absorbent reservoir; c) means retaining the absorbent reservoir in a first position above, and spaced apart from liquid-transferring relationship with the means defining a reaction zone; and d) means for moving the absorbent reservoir from the first position to a second position in liquid-transferring relationship with the means defining a reaction zone. In use, the sample is introduced to the means defining a reaction zone while the absorbent reservoir is in the first position. Then the absorbent reservoir is moved into the second position, and a plurality of the liquid reagents are contacted separately with the means defining a reaction zone and are drawn upwardly into the absorbent reservoir.

In preferred embodiments of the above aspects of the invention, the means defining a reaction zone is positioned to present a first side thereof in contact with a predetermined volume of sample in a sample well. A second side thereof (opposite said first side) is maintained in liquid-transferring relationship with the control absorbent. The control absorbent has an absorption capacity less than the predetermined sample volume, so that, once the control absorbent is loaded with sample, both sides of the means defining reaction zone are incubated with the volume of sample. For example, the means defining a reaction zone is a flat member having the two sides described above.

Other preferred embodiments of the above aspects of the invention are as follows:

A. The means defining a reaction zone comprises at least one reactant (e.g. a specific binding partner for the analyte) participating in a reaction to form the detectable product.

B. The reaction product is detected by visual inspection, and the means defining a reaction zone is visible by external inspection of the device; optionally, the device includes a contrast region surrounding the reaction zone to aid in the assay by contrasting with the reaction zone in respect to a characteristic being assayed; also optionally, the device can include an intensity scale for quantitative detection of sample analyte.

C. In devices featuring the second aspect of the invention (or those featuring both the first and the second aspects), the means defining a reaction zone is contained in a test head, and the absorbent reservoir is concentrically positioned with respect to the test head, allowing telescoping movement of the absorbent reservoir with respect to the test head The activator for moving the reservoir is recessed from the external dipstick profile.

D. The means defining a reaction zone is either integral with the control absorbent or it is attached to a face of the control absorbent E. The means defining a reaction zone defines at least two reaction regions, and the test device comprises means for isolating the reaction regions from each other. At least one reaction region may be a control region.

F. The device includes an aqueous impermeable face plate having at least one opening to allow liquid to reach the means defining a reaction zone. In order to provide a flush test head, the means defining a reaction zone comprises a flat reagent retention element having a node positioned to extend into each face plate opening. The nodes may be formed in the reaction zone, or they may be the result of a protrusion on the control absorbent pushing against the opposite side of the reaction zone.

G. The test may include a reagent pack sized and configured to supply a plurality of reagents to the reaction zone. For example, the reagent pack may include liquid reagents for generating a detectable reaction product.

H. The means defining a reaction zone is positioned at one end of an elongated dipstick, and the device further comprises a movable filter assembly positioned at the end of the dipstick. In particular, the device includes a reaction tray comprising a well adapted to receive the filter assembly on the dipstick and to retain the filter assembly as the dipstick is removed from the well.

A third aspect of the invention generally features a method for detecting an analyte in a sample by reacting the analyte with at least one liquid reagent to form a detectable reaction product. The method includes:

a) providing a test device comprising a control absorbent above, and in liquid-transferring relation with, a means defining a reaction zone, the control absorbent having a predetermined, limited, liquid-absorbing capacity; the control absorbent is in liquid-transferring relationship with the means defining a reaction zone;

b) inserting the dipstick into a vessel containing a predetermined volume of sample, with the control absorbent oriented above the means defining a reaction zone;

c) incubating the predetermined sample volume with the means defining a reaction zone to present the sample volume to both sides thereof;

d) allowing formation of the detectable reaction product; and e) detecting said reaction product.

In preferred embodiments of the third aspect of the invention, the sample volume exceeds the absorption capacity of the control absorbent, the means defining a reaction zone is positioned to present a first side thereof in contact with the predetermined sample volume and the means defining a reaction zone comprises a second side which is in liquid-transferring contact with the control absorbent. The method comprises maintaining the first side of the means defining a reaction zone in a container of the predetermined volume of sample for a time in excess of the time required to saturate the control absorbent, so as to incubate the first side of means defining a reaction zone with sample in the container, and to incubate the second side of the means defining a reaction zone with sample absorbed in the control absorbent. There is diffusional communication between the sample container and the control absorbent, through the reaction zone.

Other preferred embodiments of the third aspect of the invention feature the use a device which includes: an absorbent reservoir; means retaining the absorbent reservoir in a first position spaced apart from liquid-transferring contact with the control absorbent; and means for moving the absorbent reservoir from the first position to a second position, in liquid-transferring contact with the means defining a reaction zone. Those preferred methods include: a) incubating the sample with the means defining a reaction zone while the absorbent reservoir is in the first position; b) thereafter, moving the absorbent reservoir to the second position; and c) while the absorbent reservoir is maintained in the second position, contacting the means defining a reaction zone with at least one liquid reagent and allowing the reagent to flow through the reaction zone into the absorbent reservoir. Such a method may involve contacting the means defining a reaction zone with a second liquid reagent while maintaining the absorbent reservoir in contact with the control absorbent, and allowing the second liquid reagent to flow through the reaction zone into the absorbent reservoir.

Also, in the third aspect of the invention, the absorbent reservoir preferably is maintained in the first position for a predetermined length of time selected to control the desired reaction, whereby both the volume of sample contacted with the reaction zone and the duration of contact of the sample and reaction zone are controlled.

Another preferred method uses a device comprising a test head at one end thereof which comprises the means defining a reaction zone. In that method, the test head is oriented downwardly and is immersed in the sample and in the liquid reagents. After the detectable reaction product is formed, the device is inverted to position the test head at the top thereof for detection of the product. The means defining a reaction zone is positioned at one end of an elongated test device and a removable filter assembly is positioned around that end of the test device. The test device further comprises a reagent tray with a sample well adapted to receive the filter assembly, so that the end of the test device can be inserted in the well. Most preferably, the well contains the sample, and the method comprises: maintaining the end of the test device in the well to allow the sample to incubate with the means defining a reaction zone; removing the test device from the well while the filter assembly remains trapped in the well; and immersing the end of the test device (without the filter assembly) in a second well in the tray containing a liquid reagent.

The invention features a particularly rapid assay that is easy to use with a minimal sample volume. The test result is reliably read, with enhanced background contrast and with reliable controls. The test device is readily assembled with protection against error during assembly and use. The overall assay generally represents a significant cost savings. Since the size of the reaction zone is minimized, and flow is not wasted on regions outside the zone, the amount of reagent used is minimized The number of steps involved is reduced, thus reducing the opportunity for operator error. Mixing and measuring of reagents is avoided. Internal, self-executing controls provide increased reliability.

Other features and advantages of the invention will be apparent from the following description of the preferred embodiment thereof, from the figures, and from the claims.

DESCRIPTION OF THE PREFERRED EMBODIMENT

STRUCTURE

Figure 1:
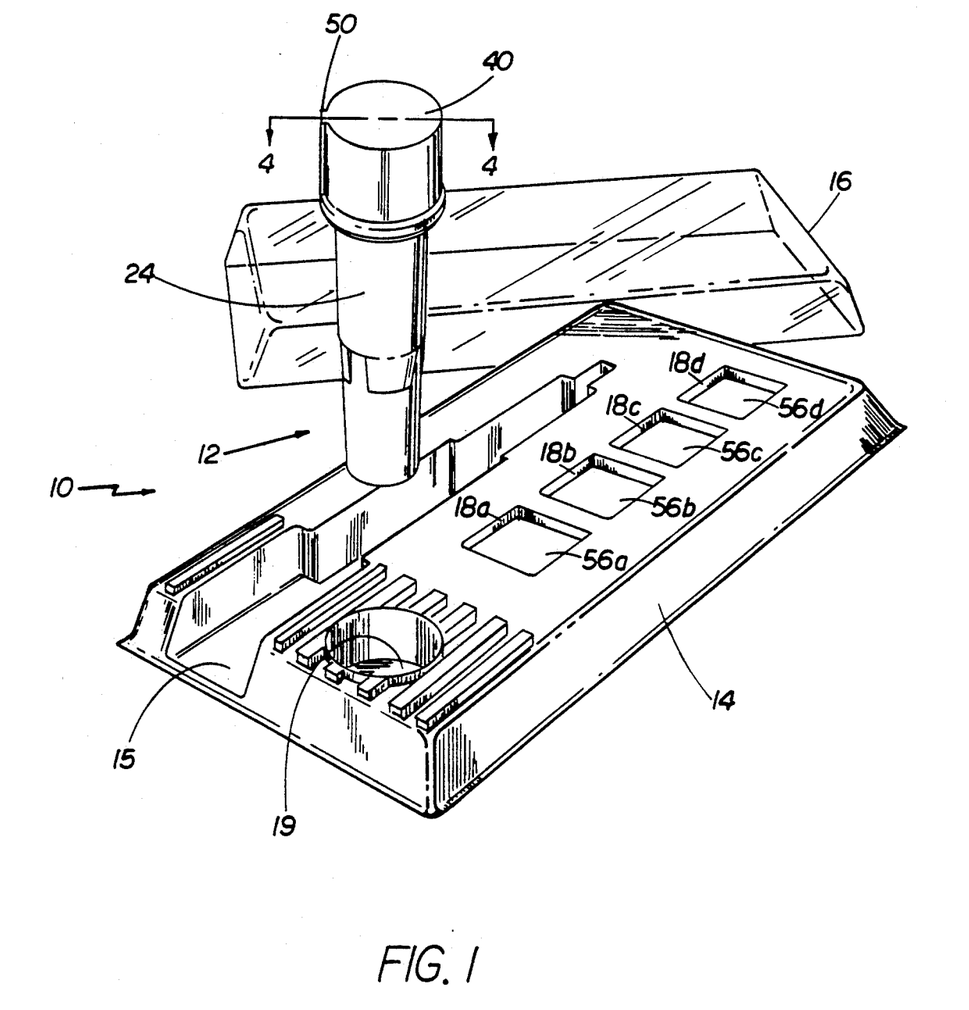
FIG. 1 is a view of an immunoassay kit.

In FIG. 1 an immunoassay kit 10 includes a dipstick 12 and a reagent tray 14 which has a clear lid 16. There are four wells 18a–18d in tray 14, described in greater detail below. Tray 14 also includes an elongated slot 15 to accommodate dipstick 12 and a circular sample well 19 to receive the sample.

In FIGS. 2-6, dipstick 12 includes a test head 20, a barrel 24, and a cap 40. Test head 20 (best shown in FIG. 6) is sized to be immersed in sample well 19 and in wells 18a–18d (where it contacts felt matrices 56a–56d). Test head 20 has three liquid-receiving openings in face 22. Round openings 21a and 21b are positive and negative control openings, respectively, as explained below. Opening 23 is the analyte detection opening. An index notch 25 is positioned opposite positive control opening 21a to indicate the proper test head orientation when reading test results.

Figures 2, 2A, 3:
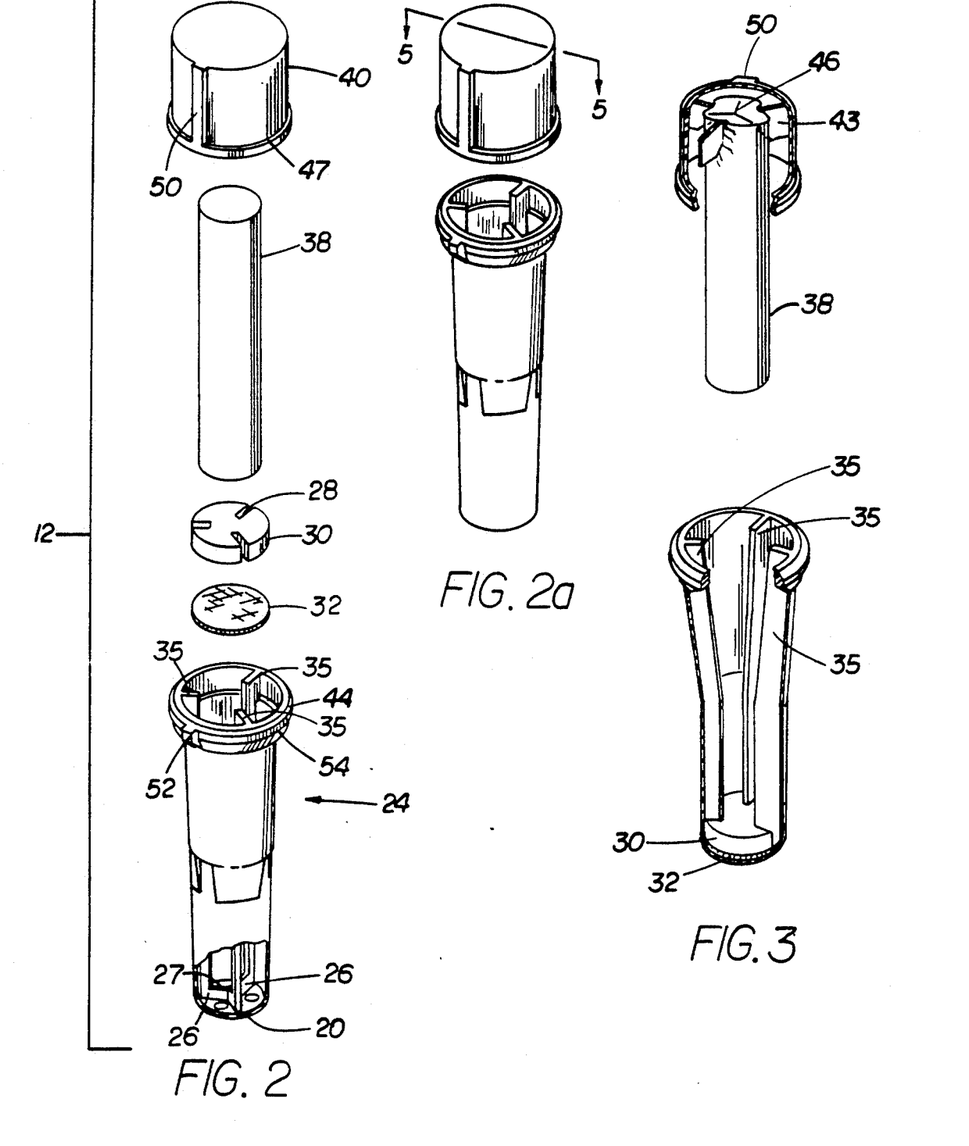
FIG. 2 is an exploded view of the dipstick of FIG. 1.
FIG. 2a is a view of the cap and barrel of the dipstick of FIG. 2, with other parts of the dipstick omitted.
FIG. 3 is a view, with parts broken away, showing assembly of the dipstick of FIG. 2.
Figure 4:
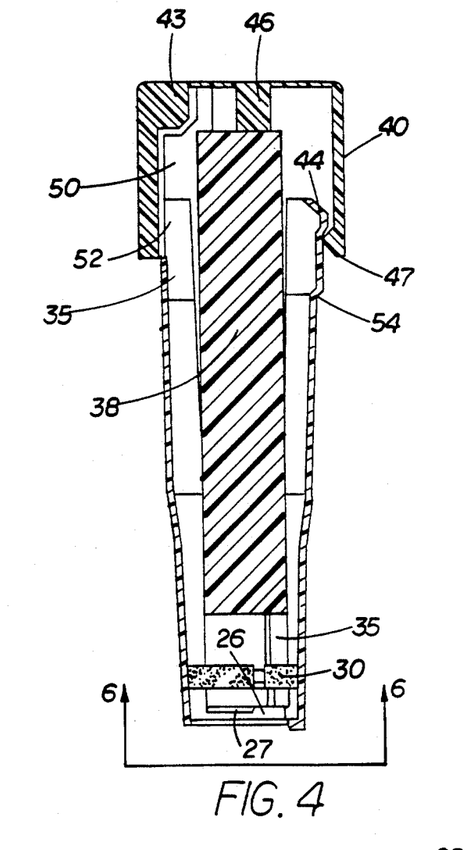
FIG. 4 is a side view of the dipstick of FIG. 2. in section, with parts omitted for clarity, taken along 4—4 of FIG. 1.
Figure 5:
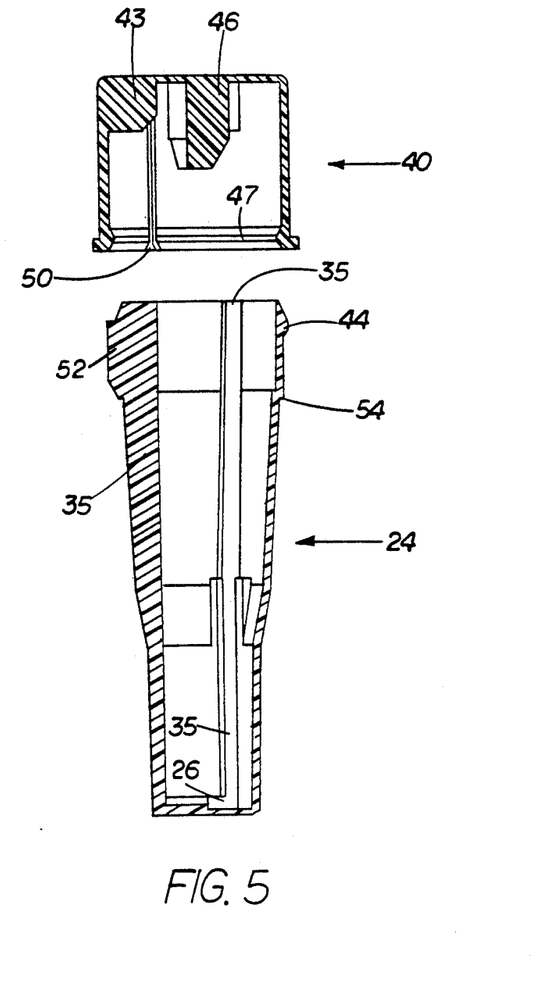
FIG. 5 is an exploded cross-section of the dipstick of FIG. 2 taken along 5—5 of FIG. 2a, with parts omitted for clarity.
Figure 6:
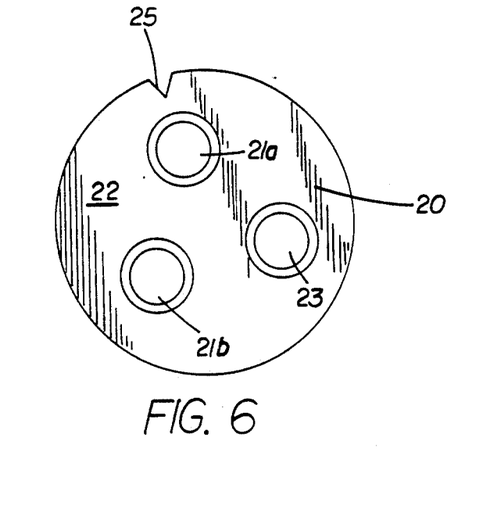
FIG. 6 is a view along 6—6 of FIG. 4.

In FIGS. 2-5, barrel 24 of the dipstick includes three axially extending fins 35 evenly spaced around the circumference of the interior of the barrel and integral with the barrel As shown in FIGS. 4 and 5, fins 35 extend to the head region of the dipstick, where they terminate in radial fins 26, which are shown in more detail in FIGS. 2 and 5. Fins 26 are shaped and positioned to fit within three radial recesses 28 in the primary (or control) absorbent 30, described below, and each terminates in a sharp edge 27, designed to pierce depth matrix 32 during assembly.

A cylindrical absorbent reservoir 38, positioned within barrel 24, is described in greater detail below. Axial ribs 35 center the absorbent reservoir. Barrel 24 also includes an indexing block 52 extending radially beyond the circumference of the barrel.

Depth matrix 32 can be a glass fiber membrane (e.g., Gelman A/E; Pall 0-10) which is capable of absorbing microparticles as described below.

Control absorbent 30 is hydrophilic polyethylene material, which has slots 28 molded in it. For each test, a desired optimum sample. volume is determined, and the control absorbent depth and porosity are selected accordingly. A typical volume of sample desired to be moved through the reaction zone is less than 400 μl and certainly less than 1 ml (most preferably less than 150-200 μl). A suitable control absorbent for a volume of 100-150 μl is a porous polyethylene (average pore size 40μ) with a diameter of 0.410 inches and a thickness of 0.100 inches. Such material is available from Porex Technology, Fairburn Ga. or Chromex Inc., Brooklyn, N.Y.

The absorbent reservoir 38 comprises drawn cellulose acetate fibers of 3.5 to 4.5 denure. The fibers may be oriented parallel to the barrel axis (along the direction of fluid movement) to provide fast wicking and thereby reduce the total assay time. The fibers are treated with a plasticizer such as triacten to stiffen them and improve flow. The absorbent reservoir should have excess capacity for the total liquid volume to be moved through the reaction zone, e.g., at least about 5 ml.

Cap 40 includes cross-members 46 and offset ribs 43 (FIG. 5) to pinch and retain absorbent reservoir 38, as shown in FIG. 4. Indexing void 50 on the interior of cap 40 mates with indexing block 52 on the exterior of barrel 24. A ridge 47 extends around the circumference of the interior of cap 40 and mates with circumferential ridges 44 and 54 on the exterior of barrel 24.

ASSEMBLY

Solid portions of the dipstick are suitable plastic such as injection molded polypropylene. The barrel and test head are molded as separate parts.

Figure 7A:
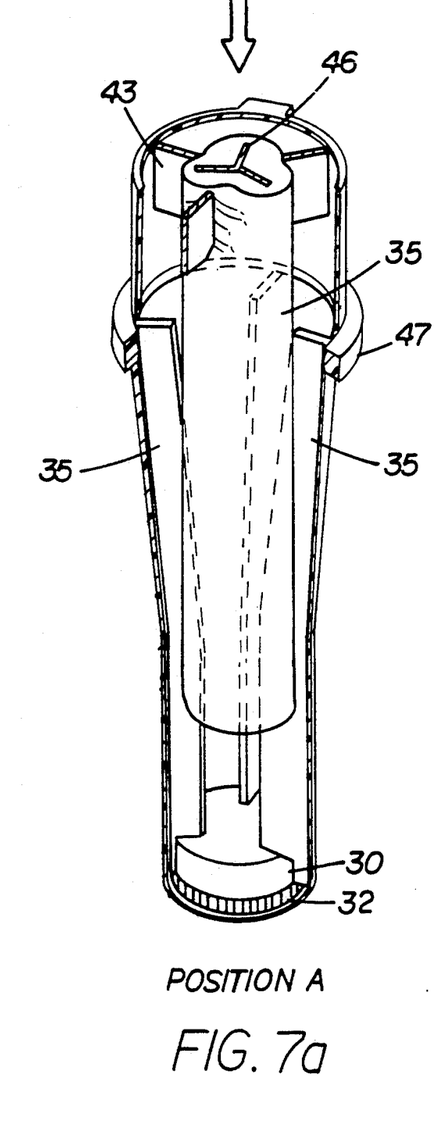
FIGS. 7A and 7B show, respectively, the two operating positions of the dipstick of FIG. 2.

Reservoir 38 is pinched between cross-members 46 and ribs 43, so that the reservoir is retained away from control absorbent 30. Cap 40 is forced over the end of barrel 24, with indexing void 50 positioned over indexing block 52. Ridge 47 is snapped over ridge 44, but not over ridge 54, so absorbent reservoir 38 is maintained apart from control absorbent 30 as shown in position A of FIG. 7.

After assembly, the microparticles are spotted through test head ports into the assay region. Specifically, latex microparticles with anti-analyte antibody can be spotted through analyte detection port 23 onto depth matrix 32. Latex particles containing either antibody to enzyme conjugate or analyte are spotted through positive control 21a. Particles non-reactive to the sample or the reagents are spotted through negative control 21b. The latex microparticles can be made of polystyrene. Proteins are immobilized on the particles by known techniques. See, e.g., Bangs, Uniform Latex Particles, Seragen Diagnostics. The particles are suspended in a buffer (e.g., 0.5%-1.0% or even 0.1-5% by weight in a standard saline buffer appropriate for the enzyme at issue) to be dropped onto the reaction zone.

USE

The user receives kit 10 with dipstick 12 nested in slot 15, and lid 16 covering tray 14. After removing the lid, sample is added to well 19 according to a protocol that will depend upon the sample and the precise nature of the assay.

Dipstick 12 is removed from the slot. At this stage, the cap 40 is retracted, and the absorbent reservoir 38 is spaced apart from the control absorbent (position A in FIG. 7).

Figure 8:
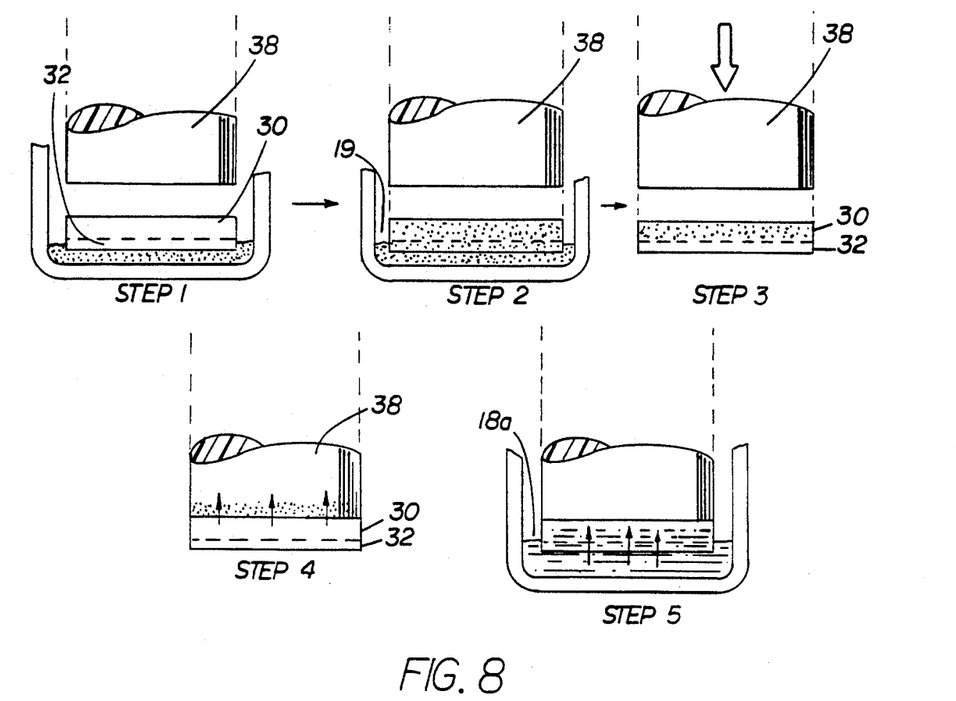
FIG. 8 shows, in highly diagrammatic fashion, five steps in an assay using the kit of FIG. 1.

The test head 20 is immersed in sample well 19 (FIG. 8, step 1). The amount of sample drawn through the reaction zone 32 is determined by control absorbent 30. Specifically, the porosity and dimensions of the control absorbent control the sample volume drawn into the reaction zone. The capacity of control absorbent 30 is limited—i.e., the control absorbent will not absorb all of the sample in well 19. Rather, once absorbent 30 is filled to capacity, sample absorption (i.e., from the receiving face of the zone to the outlet face of the zone) ceases and subsequent transfer is by diffusion. In that way, the capacity of control absorbent 30 meters the extent of flow of sample through the reaction zone predetermined (experimentally) to provide reliable analyte detection. That capacity will depend on the amount of reagent available in the reaction zone, the intensity of the parameter being detected, the level of analyte as to which discrimination is desired, sample viscosity, and the sample volume available.

Figure 7B:
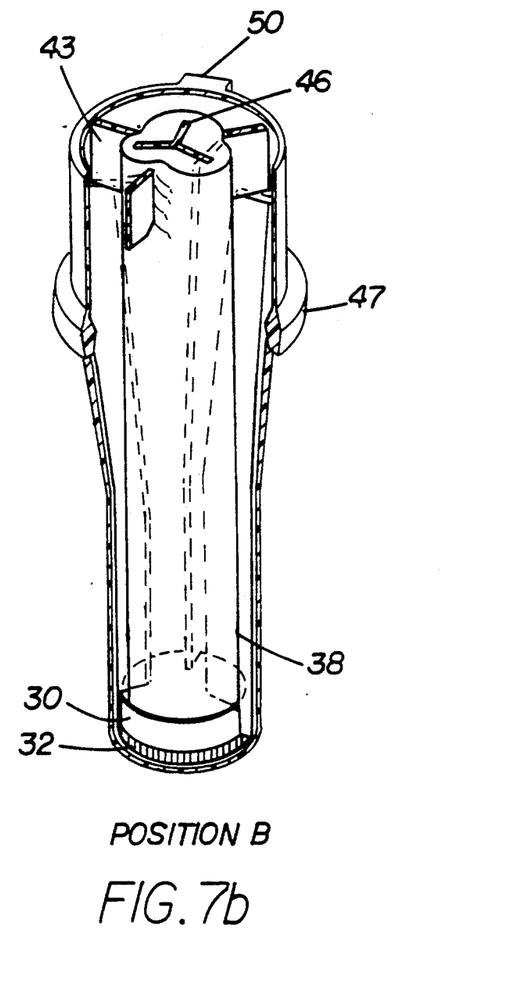

The dipstick remains in the sample long enough to absorb the desired sample volume and to allow incubation of the sample with the active reagent from e.g. 10 seconds to a few (1-5 or even more, e.g. 15) minutes (FIG. 8, step 2), the test head is removed from the sample well (FIG. 8, step 3). The user presses the cap inwardly (in the direction of the test head). As ridge 47 engages ridge 54, an audible click is produced. In this position (position B in FIG. 7), the absorbent reservoir 38 is forced in contact with the control absorbent (FIG. 8, step 4), so that liquid is wicked away from assay region 32 and control absorbent 30, into the reservoir 38.

Figure 9:
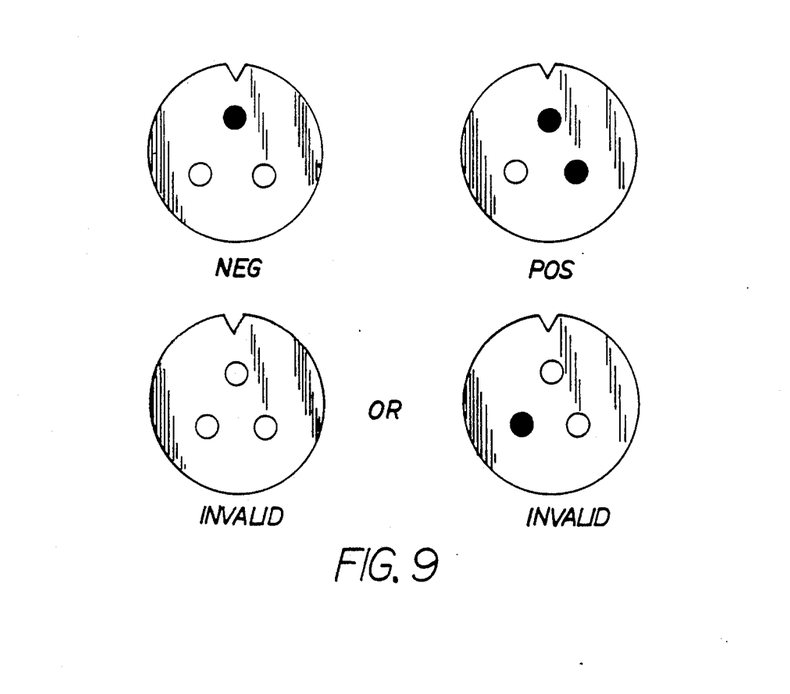
FIG. 9 depicts a key for reading the results of the assay of FIG. 8.

The dipstick is then inserted serially into reagent wells 18a through 18d (See FIG. 1 and FIG. 8, step 5). Each well is sized to hold the dipstick upright, by friction fit. Control over the amount of each reagent to be supplied to the assay region can be achieved in either of two ways: 1) by controlling the time of immersion in each well; or 2) by limiting the amount of reagent in the well and ensuring immersion long enough to absorb the entire contents of the well The color development takes place in the depth matrix, because the microspheres are trapped in the depth matrix and the colored product is on, or in proximity with, the microspheres. The results are read as shown in FIG. 9.

A specific sample enzyme-linked immunosorbent assay is described below by way of example and not as a limitation on the scope of the invention.

Anti-viral antibody, conjugated to latex microparticles by standard techniques are spotted through analyte detection port 23 onto the depth matrix 32. Similar latex microparticles containing enzyme are spotted through positive control port 21a onto assay region 32. Particles are spotted through negative control port 21b.

Reagent wells are filled with the reagents designated below and the residence time in each well is as follows:
  18a: antibody-enzyme conjugate (30 sec.–2 minutes.)
  18b: wash solution (60 sec.)
  18c: enzyme substrate (30–60 sec.)
  18d: stop solution—A solution which either stops enzyme activity, and/or precipitates the substrate by changes in pH, ionic strength, or the addition of an inhibitor Suitable systems include well known alkaline phosphatase systems and horseradish peroxidas $H_2O_2$ systems.

Each well 18a–18d contains a polypropylene or felt matrices 56a–56d which are sonically welded to the bottom of a well and pre-loaded with the reagent or wash in question. The matrices release the reagent when compacted by the test head. A foil seal over the well openings prevents liquid evaporation during storage, before removal and use of the kit.

Figure 10:
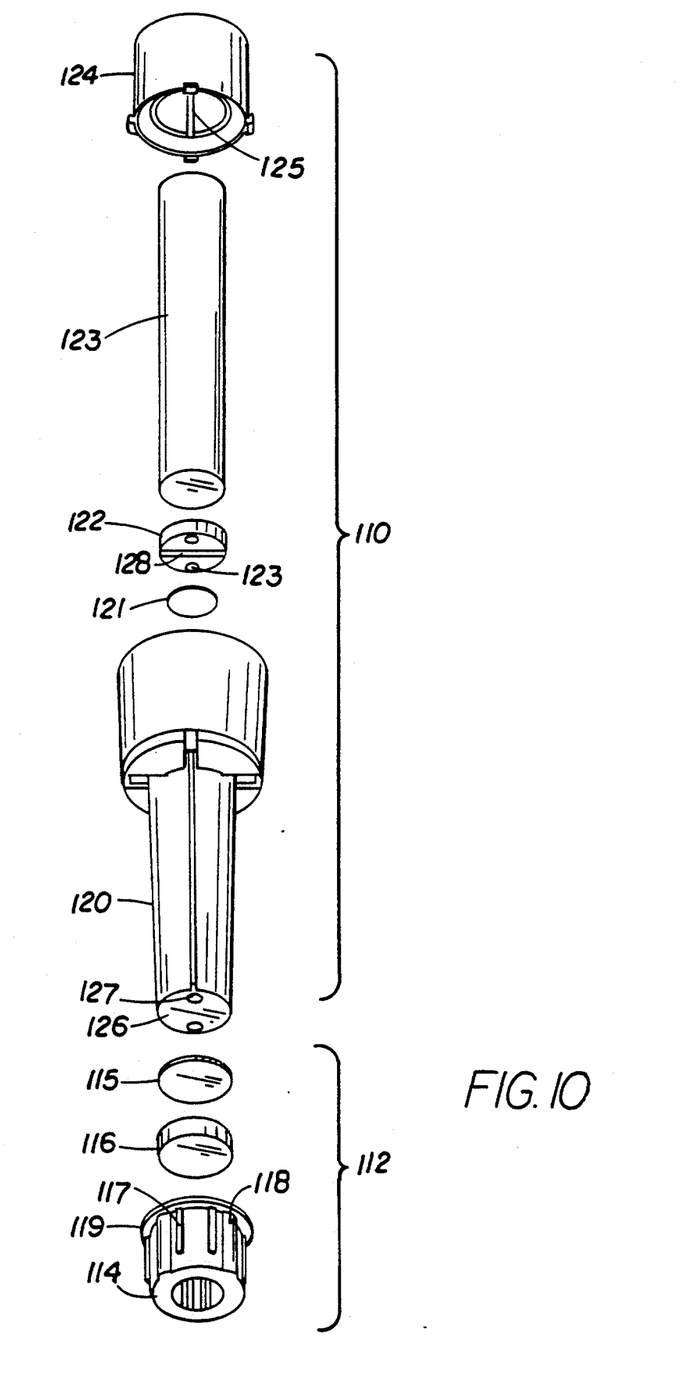
FIG. 10 depicts an exploded view of an alternative dipstick embodiment with a filter.

FIGS. 10–13 depict an alternative embodiment of a dipstick 110 used in an immunoassay kit similar to the kit depicted in FIG. 1. In FIG. 10 (an exploded view) dipstick 110 includes filter assembly 112 consisting of a filter elements 115 and 116 which are maintained in position on the head of dipstick 110 by collar 114.

Filter elements 115 and 116 can be used for a variety of filtering functions, including removal of red blood cells from blood, according to the technique of U.S. Ser. No. 905,856, filed Sept. 10, 1986, now U.S. Pat. No. 4,939,096 which is hereby incorporated by reference. Elements 116 and 115 are glass fiber filters selected for a particular application such as filtering blood cells or milk solids. Element 116 is courser than element 115, and is designed to avoid clogging of element 115.

Dipstick 110 is generally similar to dipstick 10, but it has a somewhat simplified actuation design. Body 120 contains a control absorbent 122 and a glass fiber reaction zone element 121 positioned at the head of face plate 126. Protrusions 123 on absorbent 122 force element 121 through openings 127 in face plate 126. A slot 128 in absorbent 122 receives a cutting fin (not shown)

inside body 120 which, at the time of assembly, cuts element 121 into multiple pieces to avoid cross-talk between the ports, as described above; thus, in FIG. 10, element 121 is shown prior to assembly. Reservoir absorbent 123 is retained in recessed cap 124 by fins 125.

Figure 11:
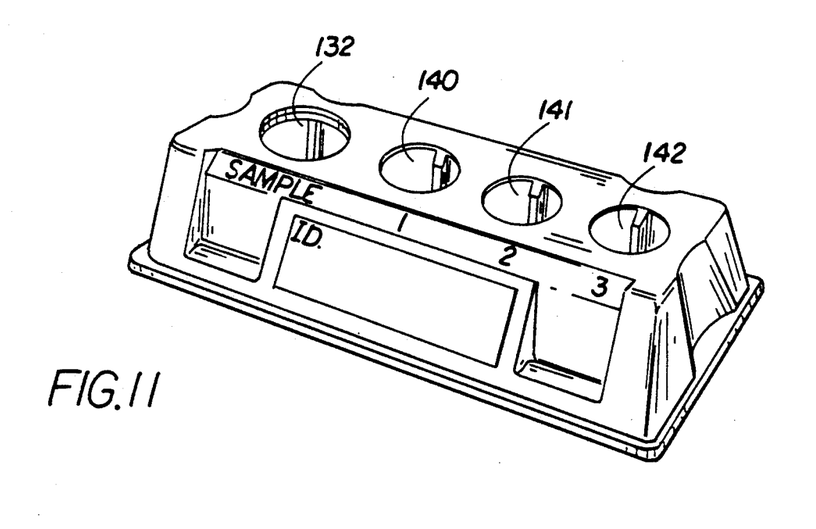
FIG. 11 is a view of the alternative dipstick of FIG. 10, in use.

FIG. 11 shows a perspective of dipstick 110, in use. Cap 124 is recessed in the barrel, even before the reservoir 123 is forced into contact with control absorbent 122 (i.e., at position A of FIG. 7). In this way, inadvertent triggering of the reservoir absorption capacity is avoided.

Figure 12:
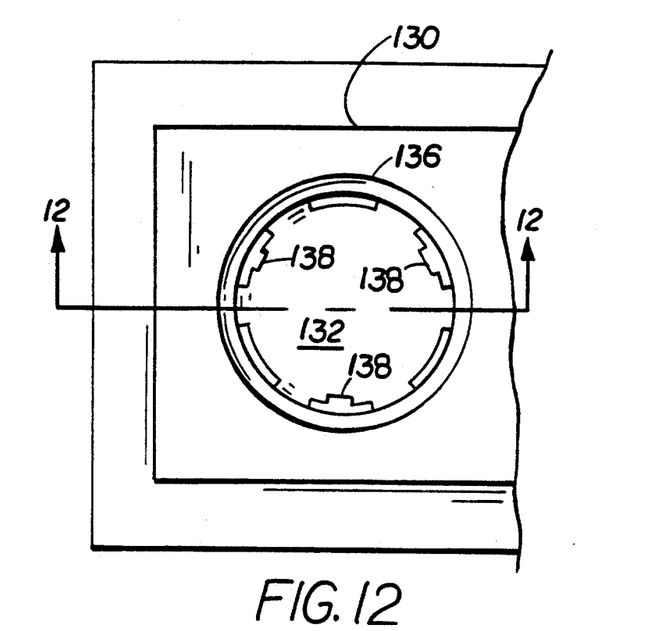
FIGS. 12 and 13 are different views of a sample tray for use with the dipstick of FIG. 10.
Figure 13:
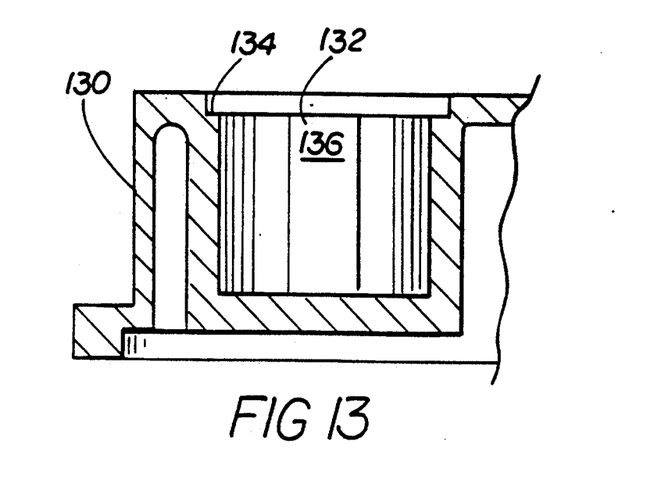

FIG. 12 and 13 show cross sections of a reagent tray 130 for use with dipstick 110. The use of the tray is similar to the procedure described above, with the exception of the sample well 132 which is designed to capture and remove filter assembly 112.

Specifically, after a measured amount of sample is added to well 132, the dipstick is inserted into that well, oriented with the filter assembly first, until the annular rim 119 on filter assembly 112 seats on ridge 134 of the well. Each of the three large external ribs 118 of assembly 112 are accommodated in cooperatively placed and sized slots 136 of the well. There is a smaller spacing rib 117 on each side of each rib 118. Three lock tabs 138 spaced evenly around the circumference of well 132 serve as dements to accommodate rim 119 as it is forced downwardly into the well. Tabs 138 spring back to lock the rim in place so that the filter is retained in well 132 after incubation with the sample.

After incubation in well 132, dipstick 110 is removed from well 132, leaving filter assembly 112 in well 132. Reservoir absorbent 123 is spaced apart from the control absorbent during this incubation procedure. To bring reservoir absorbent 123 in contact with control absorbent 122 (and thereby bring it in liquid-transferring relationship with reaction zone element 121), cap 124 is pressed forceably inward. Even in the retracted position, cap 124 is recessed—i.e., it does not extend past the end of body 120—to avoid inadvertent actuation. The remainder of the wash and reagent steps are performed in wells 140-142 as described above, by immersing the face plate 126 of dipstick body 110 in each well, sequentially As described above, the result is read on faceplate 126 by inverting the dipstick.

OTHER EMBODIMENTS

Other embodiments are within the following claims. For example, the test head can be a separate piece from the barrel. The control absorbent and depth matrix can be manufactured as a single element. For example, an absorbent porous polyethylene substrate can be constructed to have constricted pores on the top surface using a cellulosic material.

The test tray can be packaged in a shrink-wrap plastic film, omitting the cover. The test tray can be modified by changing the spacing and location of the wells. For example, sample well 19 can be moved to one end of the dipstick slot 15 and wells 18a-18d can be spaced apart, with a groove included between each well to contain liquid that drips and avoid contaminating the wells.

A range of immunoassay techniques are performed with the device, including radioactive and fluorescent techniques as well as the colorimetric technique described in this patent application. The size of the device can be adjusted depending on assay volume. A pre-filter can be used to remove undesired elements of the sample that hinder the assay, e.g. red blood cells in a whole blood assay.

The number of openings or ports in the test head can be increased, e g., multiple assays can be performed on the same sample, by spotting different analyte binding agents in different openings.

The test can be read by automated reading apparatus, as well as by visual inspection.

What is claimed is:

1. A dipstick test device for detecting an analyte in a liquid sample by treating the analyte with at least one liquid reagent to form a detectable reaction product, said dipstick of said test device comprising:
   a) means defining an aqueous permeable, aqueous insoluble reaction zone, positioned at one end of an elongated dipstick and adapted to retain said detectable reaction product;
   b) a control absorbent in liquid-transferring relation with the means defining the reaction zone, said control absorbent having a predetermined, limited liquid-absorbing capacity, said dipstick being sized and configured for insertion into a vessel containing said sample, whereby said control absorbent fills to capacity with sample and said means defining a reaction zone incubates with said sample;
   c) a re-movable filter assembly positioned at said end of said dipstick; and
   d) a reaction tray comprising a well adapted to receive said filter assembly on said dipstick and to retain said filter assembly as said dipstick is removed.

2. The test device of claim 1, said test device further comprising:
   e) an absorbent reservoir;
   f) means retaining said absorbent reservoir in a first position above and spaced apart from liquid-transferring relationship with said means defining said reaction zone; and
   g) means for moving said absorbent reservoir from said first position to a second position in liquid-transferring relationship with the means defining said reaction zone.

3. The test device of claim 2, wherein said means defining a reaction zone is contained in a test head, and said absorbent reservoir is concentrically positioned with respect to said test head, allowing telescoping movement of said absorbent reservoir with respect to said test head.

4. The test device of claim 2 wherein said means for moving said absorbent reservoir comprises an activator that is recessed from the external dipstick profile.

5. The test device of claim 1 or claim 2 wherein said control absorbent is positioned above said means defining a reaction zone, said device further comprising a sample well, said means defining a reaction zone being positioned in said dipstick so that when the dipstick is inserted in the sample well containing a predetermined volume of sample, a first side of the means defining the reaction zone contacts the sample, and a second side of the means defining a reaction zone, which is opposite said first side, and is maintained in liquid transferring relationship with said control absorbent, said control absorbent having an absorption capacity less than said predetermined sample volume, whereby both said first and said seocnd sides of said means defining a reaction zone are incubated with said volume of sample when said dipstick is inserted in said well.

6. The device of claim 5 wherein said first side of said means defining a reaction zone and said second side thereof are opposite surfaces of a flat member.

7. The device of claim 1 or claim 2 wherein said means defining a reaction zone comprises at least one reactant participating in a reaction to form said detectable product.

8. The device of claim 1 or claim 2 wherein said reaction product is detected by visual inspection after said filter assembly is removed and said means defining a reaction zone is visible by external inspection of said device.

9. The device of claim 8 further comprising a means defining a contrast region surrounding said reaction zone to aid in said detection by contrasting with said reaction zone in respect to a characteristic being assayed.

10. The device of claim 9 further comprising an intensity scale for quantitive detection of sample analyte.

11. The test device of claim 1 or claim 2 wherein said means defining a reaction zone is integral with said control absorbent.

12. The test device of claim 1 or claim 2 wherein said means defining a reaction zone is attached to a face of said control absorbent.

13. The test device of claim 1 or claim 2 wherein said means defining a reaction zone defines at least two reaction regions and said test device comprises means for isolating said reaction regions from each other.

14. The test device of claim 13 wherein at least one of said reaction regions is a control region.

15. The test device of claim 1 or claim 2 further comprising an aqueous impermeable face plate having at least one opening to allow liquid to reach said means defining a reaction zone.

16. The test device of claim 15 wherein said means defining a reaction zone comprises a flat reagent retention element having a protrusion positioned to extending into an opening in said face plate.

17. The test device of claim 15 wherein said control absorbent is shaped to present a node that forces said means defining a reaction zone to protrude into an opening in said face plate.

18. The test device of claim 1 or claim 2 further comprising a reagent pack sized and configured to supply a plurality of reagents to said reaction zone.

19. The test device of claim 1 or claim 2 wherein said means defining a reaction zone comprises a specific binding partner for said analyte.

* * * * *